US010088667B2

(12) United States Patent
Narita

(10) Patent No.: US 10,088,667 B2
(45) Date of Patent: Oct. 2, 2018

(54) ELECTRONIC ENDOSCOPE APPARATUS HAVING CONNECTORS WITH CONTACT PARTS

(71) Applicant: FUJIFILM Corporation, Tokyo (JP)

(72) Inventor: Satoshi Narita, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 141 days.

(21) Appl. No.: 15/229,971

(22) Filed: Aug. 5, 2016

(65) Prior Publication Data

US 2016/0341952 A1  Nov. 24, 2016

Related U.S. Application Data

(63) Continuation of application No. PCT/JP2014/078547, filed on Oct. 28, 2014.

(30) Foreign Application Priority Data

Mar. 27, 2014  (JP) ................................. 2014-066320

(51) Int. Cl.
*A61B 1/00* (2006.01)
*G02B 23/24* (2006.01)
(Continued)

(52) U.S. Cl.
CPC ...... *G02B 23/2476* (2013.01); *A61B 1/00124* (2013.01); *A61B 1/00126* (2013.01);
(Continued)

(58) Field of Classification Search
CPC ... A61B 1/00124; A61B 1/00126; A61B 1/04; A61B 1/00128; A61B 1/00121;
(Continued)

(56) References Cited

U.S. PATENT DOCUMENTS 3,636,494 A * 1/1972 Smith .................. H01R 13/652
                                                              439/107
3,829,814 A * 8/1974 Straus ..................... E21B 17/028
                                                              439/101
(Continued)

FOREIGN PATENT DOCUMENTS

JP    4-146719 A    5/1992
JP    7-326427 A   12/1995
(Continued)

OTHER PUBLICATIONS

Extended European Search Report, dated Feb. 16, 2017, for European Application No. 14887151.0.
(Continued)

*Primary Examiner* — John P Leubecker
(74) *Attorney, Agent, or Firm* — Birch, Stewart, Kolasch & Birch, LLP

(57) ABSTRACT

An electronic-endoscope-apparatus 1 comprises an electronic-endoscope 2 and a processor device 3 that transmits and receives power and signals between the electronic-endoscope 2 and itself The electronic-endoscope 2 and the processor device 3 have connectors 13 and 14 that are connected to each other, respectively. The connectors 13 and 14 include input/output units 31 and 33 that transmit and receive power and signals, and contact parts 32 and 34 that electrically connect a ground of the electronic endoscope 2 to a ground of the processor device 3. When connection between the connectors 13 and 14 is released, contact between the contact parts 32 and 34 is released after coupling between the input/output units 31 and 33 is released and the transmission and reception of power become impossible.

12 Claims, 10 Drawing Sheets

(51) Int. Cl.
*H04N 5/225* (2006.01)
*A61B 1/04* (2006.01)

(52) U.S. Cl.
CPC ........ *H04N 5/2256* (2013.01); *A61B 1/00016* (2013.01); *A61B 1/04* (2013.01); *H04N 2005/2255* (2013.01)

(58) Field of Classification Search
CPC ............ A61B 1/00016; A61B 1/00029; H04N 5/2256; H04N 2005/2255; G02B 23/2476
USPC ........................................................ 600/134
See application file for complete search history.

(56) References Cited

U.S. PATENT DOCUMENTS

| | | | | |
|---|---|---|---|---|
| 4,140,358 | A * | 2/1979 | Marechal | H01R 13/447 439/139 |
| 4,974,075 | A * | 11/1990 | Nakajima | A61B 1/00124 348/75 |
| 5,056,503 | A * | 10/1991 | Nagasaki | A61B 1/00179 600/104 |
| 5,225,958 | A | 7/1993 | Nakamura | |
| 5,441,043 | A * | 8/1995 | Wood | A61B 1/04 348/75 |
| 5,543,831 | A * | 8/1996 | Tsuji | H04N 7/183 128/901 |
| 5,569,158 | A * | 10/1996 | Suzuki | A61B 1/00114 348/76 |
| 5,716,323 | A * | 2/1998 | Lee | H04N 5/23203 348/76 |
| 5,810,620 | A | 9/1998 | Kobayashi et al. | |
| 5,810,714 | A * | 9/1998 | Takamura | A61B 1/05 600/130 |
| 6,099,465 | A * | 8/2000 | Inoue | A61B 1/05 348/75 |
| 6,319,197 | B1 * | 11/2001 | Tsuji | H04N 7/183 348/E7.087 |
| 6,371,907 | B1 * | 4/2002 | Hasegawa | G02B 23/2476 600/102 |
| 2006/0116550 | A1 | 6/2006 | Noguchi et al. | |
| 2006/0116552 | A1 * | 6/2006 | Noguchi | A61B 1/00121 600/159 |
| 2013/0035550 | A1 * | 2/2013 | Watanabe | G02B 6/4298 600/132 |

FOREIGN PATENT DOCUMENTS

| | | |
|---|---|---|
| JP | 10-151113 A | 6/1998 |
| JP | 10-155740 A | 6/1998 |
| JP | 10-162903 A | 6/1998 |
| JP | 2000-92478 A | 3/2000 |
| JP | 2013-208187 A | 10/2013 |

OTHER PUBLICATIONS

International Search Report for PCT/JP2014/078547 (PCT/ISA/210) dated Feb. 3, 2015.
Written Opinion of the International Searching Authority for PCT/JP2014/078547 (PCT/ISA/237) dated Feb. 3, 2015.
Japanese Notification of Reasons for Refusal dated Apr. 11, 2017, for corresponding Japanese Application No. 2016-509894, with English translation.
Chinese Office Action and Search Report dated Jun. 1, 2017, for Chinese Application No. 201480076110.4, with an English translation of the Office Action.
Chinese Office Action and Search Report for corresponding Chinese Application No. 201480076110.4, dated Nov. 28, 2017, with an English translation of the Office Action.
English Translation of International Preliminary Report on Patentability (including PCT/IB/373 and PCT/ISA/237) for PCT/JP2014/078547, dated Sep. 27, 2016.
European Office Communication pursuant to Article 94(3) EPC dated Mar. 8, 2018 for corresponding European Application No. 14887151.0.

* cited by examiner

ELECTRONIC ENDOSCOPE APPARATUS HAVING CONNECTORS WITH CONTACT PARTS

CROSS-REFERENCE TO RELATED APPLICATIONS

This application is a Continuation of PCT International Application No. PCT/JP2014/078547 filed on Oct. 28, 2014, which claims priority under 35 U.S.C § 119 (a) to Japanese Patent Application No. 2014-066320 filed on Mar. 27, 2014. Each of the above application(s) is hereby expressly incorporated by reference, in its entirety, into the present application.

BACKGROUND OF THE INVENTION

1. Field of the Invention

The present invention relates to an electronic endoscope apparatus.

2. Description of the Related Art

An electronic endoscope on which an electronic device such as an imaging device is mounted is connected to a processor device, and transmits and receives power and signals of the electronic device between the processor device and itself.

In regard to the transmission and reception of power and signals between the electronic endoscope and the processor device, connectors of the electronic endoscope and the processor device are typically provided with terminal groups, which are connected to each other, and power and signals are transmitted through these terminal groups.

Further, electronic endoscope apparatuses, which are adapted so as to prevent damage to electronic devices as a concern in a case in which signals are applied before power is supplied to the electronic devices, are also known (for example, see JP1995-326427A (JP-H07-326427A) and JP2000-92478A).

The electronic endoscope apparatus disclosed in JP1995-326427A (JP-H07-326427A) is adapted so that ground terminals and power terminals are connected before the connection of signal terminals and the connection of the ground terminals and the power terminals is released after the release of the connection of the signal terminals.

The electronic endoscope apparatus disclosed in JP2000-92478A is adapted so that a switch interlocking with the connection of connectors is provided on a power line and power starts to be supplied to the power line after ground terminals and power terminals are connected.

Further, in electronic endoscope apparatuses that transmit and receive power and signals by the connection of terminal groups of connectors, a waterproof treatment for the terminal group of the connector of an electronic endoscope is necessary at the time of cleaning and disinfection of the electronic endoscope. Accordingly, electronic endoscope apparatuses, which transmit and receive power and signals between an electronic endoscope and a processor device while insulation between the electronic endoscope and the processor device is maintained by using a pair of coils, light-emitting/receiving elements, or the like instead of the terminal groups, are also known (for example, see JP1998-155740A (JP-H10-155740A) and JP2013-208187A).

SUMMARY OF THE INVENTION

For example, immediately after a power supply of the processor device is turned off or the connection between the connector of the electronic endoscope and the connector of the processor device is released so that the supply of power to the electronic endoscope from the processor device is cut off, residual charge remains in the electronic device of the electronic endoscope. Residual charge is discharged by, for example, a resistor of a circuit. If a ground of the electronic endoscope is floating in this case, residual charge is discharged along a path that is different from an assumed path and at a timing that is different from an assumed timing. For this reason, there is a concern that the electronic device may malfunction.

Since an electronic endoscope apparatus, which transmits and receives power and signals between the electronic endoscope and the processor device while insulation between the electronic endoscope and the processor device is maintained as in the electronic endoscope apparatuses disclosed in JP1998-155740A (JP-H10-155740A) and JP2013-208187A, does not include terminal groups of connectors in order to make a waterproof treatment unnecessary, the ground of the electronic endoscope is separated and is floating from the ground of the processor device. For this reason, the electronic endoscope apparatus, which transmits and receives power and signals while insulation between the electronic endoscope and the processor device is maintained, is insufficient for residual charge.

The invention has been made in consideration of the above-mentioned circumstances, and an object of the invention is to provide an electronic endoscope apparatus in which the protection of an electronic device mounted on an electronic endoscope is enhanced.

An electronic endoscope apparatus comprises an electronic endoscope, and a processor device that transmits and receives power and signals between the electronic endoscope and itself. The electronic endoscope and the processor device have connectors that are connected to each other, respectively. The connectors include input/output units that transmit and receive power and signals, and contact parts that electrically connect a ground of the electronic endoscope to a ground of the processor device. When connection between the connectors is released, contact between the contact parts is released after coupling between the input/output units is released and the transmission and reception of power become impossible.

According to the invention, it is possible to enhance the protection of the electronic device mounted on the electronic endoscope.

DESCRIPTION OF THE PREFERRED EMBODIMENTS

A preferred embodiment of the invention will be described below with reference to the drawings.

Figure 1:
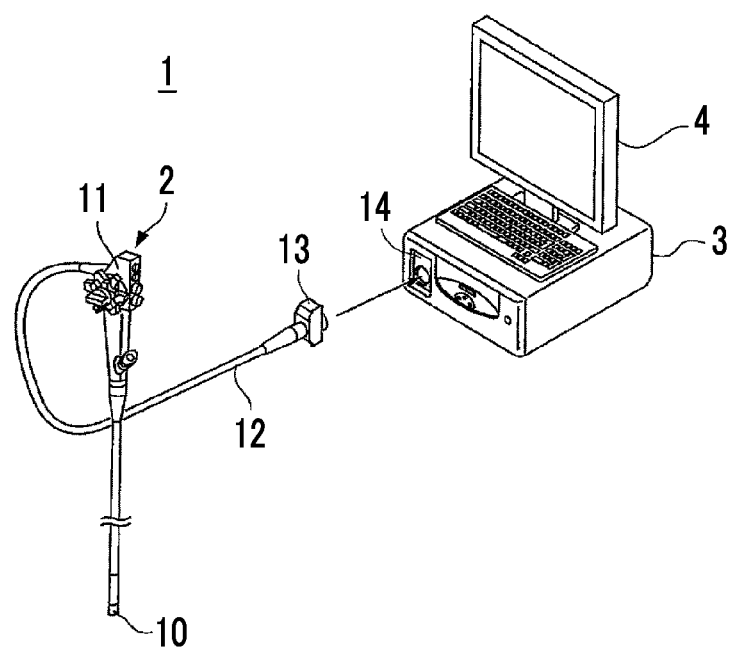
FIG. 1 is an appearance diagram of an example of an electronic endoscope apparatus that is used to illustrate an embodiment of the invention.

FIG. 1 shows the structure of an example of an electronic endoscope apparatus that is used to illustrate an embodiment of the invention.

The electronic endoscope apparatus 1 comprises an electronic endoscope 2, a processor device 3, and a monitor 4 that is connected to the processor device 3.

The electronic endoscope 2 has an insertion part 10 that is inserted into a subject, an operation part 11 that is connected to the insertion part 10, and a universal cord 12 that extends from the operation part 11. A connector 13 is provided at the end of the universal cord 12, and the connector 13 is connected to a connector 14 that is provided in the processor device 3. Accordingly, the electronic endoscope 2 and the processor device 3 are connected to each other through both the connectors 13 and 14.

Figure 2:
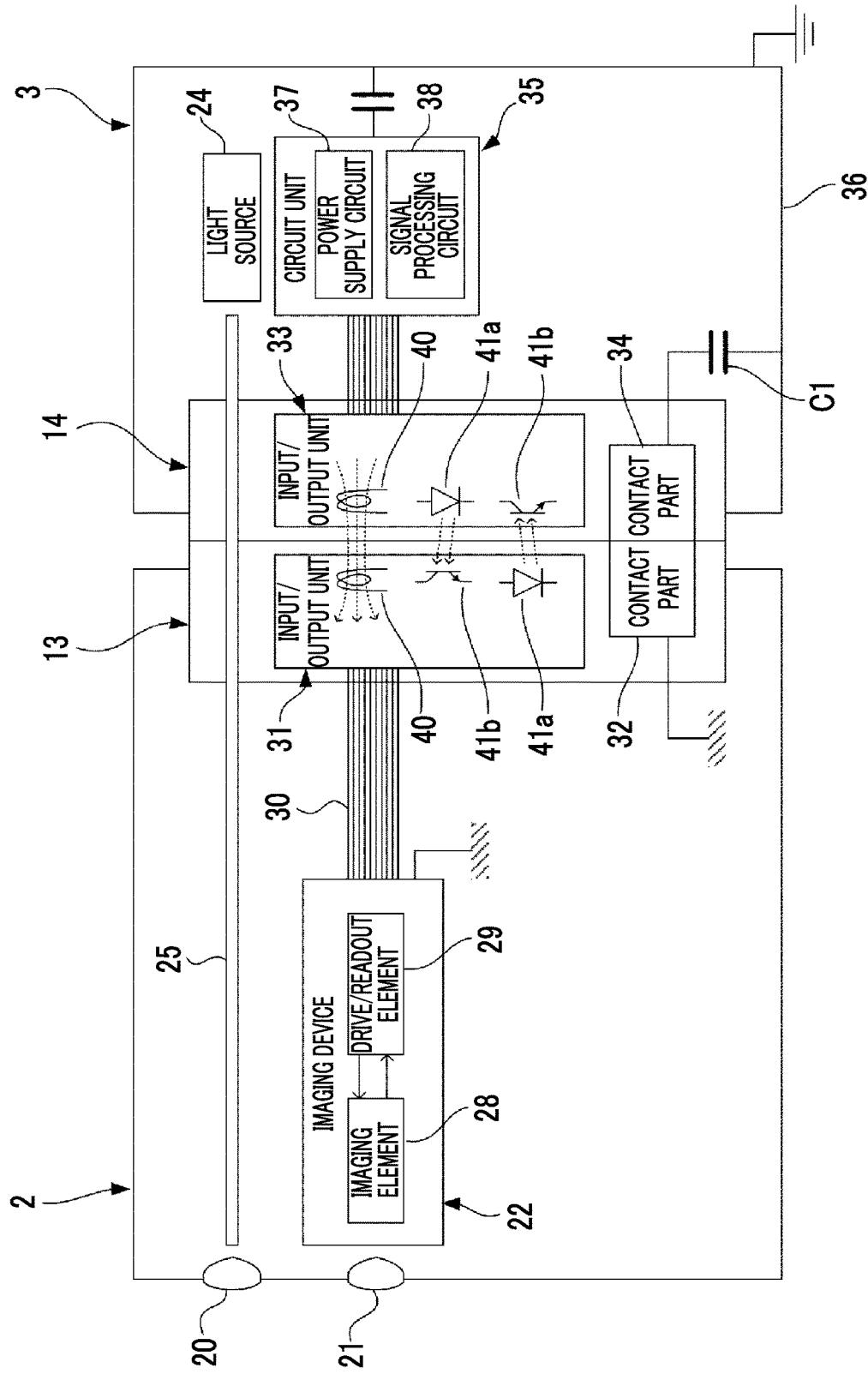
FIG. 2 is a block diagram of the electronic endoscope apparatus of FIG. 1.

FIG. 2 shows functional blocks of the electronic endoscope apparatus 1.

An illumination optical system 20 that applies illumination light, an objective optical system 21, and an imaging device 22 that receives an image formed by the objective optical system 21 are provided at a tip portion of the insertion part 10 of the electronic endoscope 2.

The illumination light, which is applied from the illumination optical system 20, is generated by a light source 24 provided in the processor device 3, and is guided to the illumination optical system 20 from the light source 24 by a light guide 25 that is included in the universal cord 12 (see FIG. 1).

The imaging device 22 comprises an imaging element 28, such as a CCD (Charge Coupled Device) image sensor or a CMOS (Complementary Metal-Oxide Semiconductor) image sensor, and a drive/readout circuit 29 that drives the imaging element 28 and reads out image signals from the imaging element 28. The drive/readout circuit 29 comprises, for example, a driver of the imaging element 28, an amplifier that amplifies image signals read out from the imaging element 28, an A/D converter that converts image signals into digital signals and outputs the digital signals, and the like.

The operating power of the imaging element 28 and the drive/readout circuit 29, control signals that are input to the drive/readout circuit 29, and image signals that are output from the drive/readout circuit 29 are transmitted through a wiring group 30, which is included in the universal cord 12, and are transmitted and received between the electronic endoscope 2 and the processor device 3 through the connectors 13 and 14.

An internal power supply, such as a battery for temporarily storing power supplied from the processor device 3, may be mounted on the electronic endoscope 2 so that power is supplied to the imaging element 28 and the drive/readout circuit 29 from the internal power supply, but the internal power supply is not mounted in an example shown in the drawings.

The connector 13 is provided with an input/output unit 31 that transmits and receives the power and signals between itself and the connector 14 of the processor device 3 and a contact part 32 that is connected to the ground of the electronic endoscope 2.

The processor device 3 has an input/output unit 33, a contact part 34, and a circuit unit 35.

The input/output unit 33 is provided in the connector 14, and the power and signals are transmitted and received between the connector 14 and the connector 13 of the electronic endoscope 2 that is connected to the connector 14. The contact part 34 is also provided in the connector 14, and is connected to a housing (ground) 36 of the grounded processor device 3 through a capacitor Cl.

The circuit unit 35 has, for example, a power supply circuit 37 that generates power to be supplied to the imaging element 28 and the drive/readout circuit 29 from a commercial power supply (not shown), and a signal processing circuit 38 that processes signals of the drive/readout circuit 29. The signal processing circuit 38 comprises, for example, a control circuit that controls the operation of the drive/readout circuit 29, an image processing circuit that generates image data by performing various kinds of signal processing, such as white balance correction, on the image signals, and the like. The image data, which are generated by the signal processing circuit 38, are displayed in a monitor 4 (see FIG. 1).

The input/output unit 31 of the connector 13 and the input/output unit 33 of the connector 14 are insulated from each other, and transmit and receive power and signals. In this specification, "insulated" means that conductors for transmitting power and signals are separated from each other, and the conductors are separated from each other between the input/output units 31 and 33.

In the embodiment shown in the drawings, coils 40 are provided in the input/output units 31 and 33, respectively. The pair of coils 40 are disposed so as to face each other without being in contact with each other in a state in which the connectors 13 and 14 are connected to each other; and transmit power by using electromagnetic induction while insulation between the coils 40 is kept.

Further, a light-emitting element 41a is provided on a signal output side of each of the input/output units 31 and 33 and a light-receiving element 41b is provided on an input side thereof. A pair of the light-emitting element 41a and the light-receiving element 41b are disposed so as to face each other with or without being in contact with each other in a state in which the connectors 13 and 14 are connected to each other; and transmit signals by using light while insulation between the light-emitting element 41a and the light-receiving element 41b is kept.

The transmission and reception of power and signals, which are performed while insulation is kept, are not limited to the above-mentioned method. For example, a magnetic resonance method in which the coils 40 are used as a resonator can also be used to transmit and receive power, and radio communication can also be used to transmit and receive signals.

Meanwhile, the contact part 32 of the connector 13 and the contact part 34 of the connector 14 come into contact with each other in a state in which the connectors 13 and 14 are connected to each other, so that a ground of the electronic endoscope 2 and the housing 36 of the processor device 3 are electrically connected to each other.

Since the ground of the electronic endoscope 2 and the housing 36 of the processor device 3 are electrically connected to each other, noises, which are applied to the electronic endoscope 2, such as radiation noises or electrostatic noises of a high-frequency treatment tool, flow in the housing 36 of the processor device 3 from the ground of the electronic endoscope 2. Accordingly, an influence of noises on the electronic endoscope 2 is reduced. Particularly, since the housing 36 is grounded in this embodiment, noises are promptly removed from the electronic endoscope 2 and the processor device 3. Accordingly, it is possible to suppress the malfunction of electronic devices, such as the imaging element 28 and the drive/readout circuit 29, which are mounted on the electronic endoscope 2.

Further, a capacitor C1 is interposed between the contact part 34 of the connector 14 and the housing 36 of the processor device 3. Accordingly, the ground of the electronic endoscope 2 is electrically connected to the housing 36 in an AC manner by capacitive coupling and is floating from the housing 36 in a DC manner. Therefore, it is possible to cut off current, which flows in a subject via the electronic endoscope 2 from the processor device 3 comprising the power supply circuit 37, without inhibiting noises, which have a high frequency, from moving to the housing 36.

Furthermore, the ground of the input/output unit 33 and the ground of the circuit unit 35 including the power supply circuit 37 are also connected to the housing 36 of the processor device 3, but the input/output unit 33 is insulated from the electronic endoscope 2. Accordingly, the ground of the input/output unit 33 can be in common with the ground of the circuit unit 35. Accordingly, insulating means, such as a transformer or a photocoupler, for insulating the input/output unit 33 from the circuit unit 35 does not need to be separately provided.

The imaging device 22 (the imaging element 28 and the drive/readout circuit 29) has been exemplified as an electronic device, which is mounted on the electronic endoscope 2, in the above-mentioned electronic endoscope apparatus 1. However, the electronic device mounted on the electronic endoscope 2 is not limited to the imaging device 22. For example, the above-mentioned electronic endoscope apparatus 1 has been adapted so that illumination light generated by the light source 24 of the processor device 3 is guided to the tip portion of the insertion part 10 of the electronic endoscope 2 by the light guide 25 and is emitted from the illumination optical system 20. However, an LED (Light Emitting Diode) and a drive circuit for the LED can be provided at the tip portion of the insertion part 10 and illumination light can also be generated by the LED.

Figure 3:
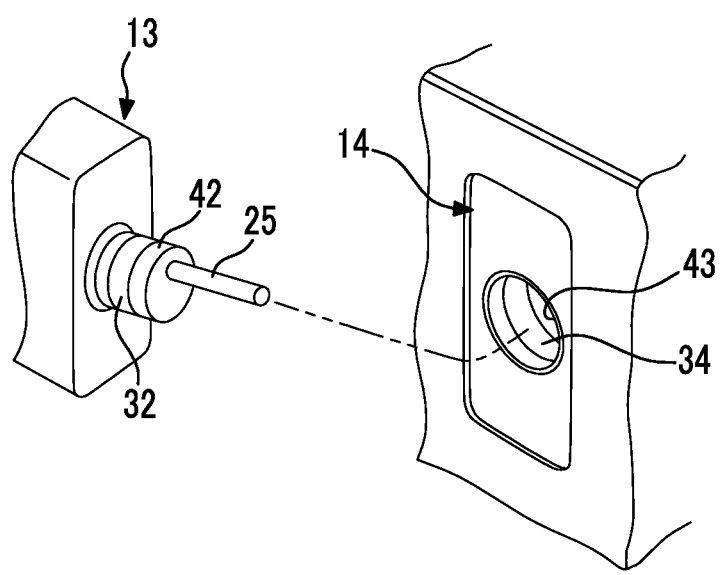
FIG. 3 is a plan view showing the structures of respective connectors of an electronic endoscope and a processor device of the electronic endoscope apparatus of FIG. 1.
Figure 4:
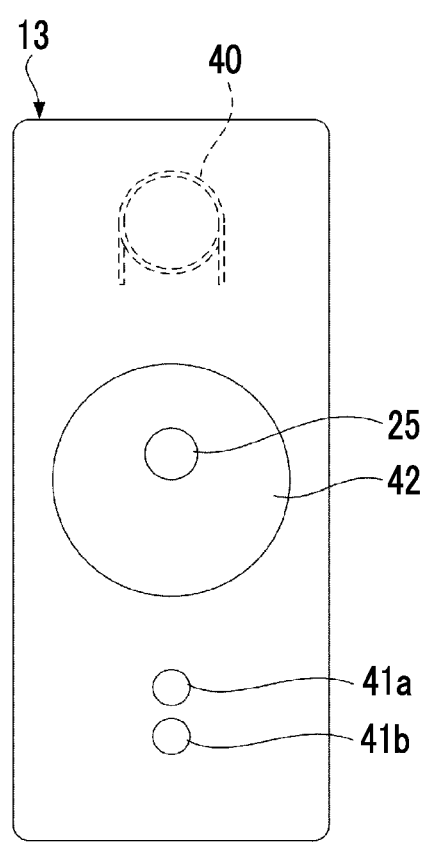
FIG. 4 is a front view of the connector of the electronic endoscope of FIG. 3.

FIGS. 3 and 4 show the structures of the connector 13 of the electronic endoscope 2 and the connector 14 of the processor device 3.

The connector 13 of the electronic endoscope 2 has a fitting portion 42 that is formed so as to protrude, and the connector 14 of the processor device 3 has a fitting portion 43 that is formed so as to be recessed. The fitting portions 42 and 43 are fitted to each other with the connection between the connectors 13 and 14, and the fitting portion 42 of the connector 13 is covered with the fitting portion 43 of the connector 14.

In the embodiment shown in the drawings, the protruding fitting portion 42 is provided at a substantially central portion of the connector 13, and an end portion of the light guide 25, which guides illumination light, is held by the fitting portion 42. Further, the coil 40, which transmits and receives power, is provided in one side portion of both side portions of the connector 13 between which the fitting portion 42 is interposed, and the light-emitting element 41a and the light-receiving element 41b, which transmit and receive signals, are provided in the other side portion thereof. The disposition of the fitting portion 42 in the connector 13 and the disposition of the light guide 25, the coil 40, the light-emitting element 41a, and the light-receiving element 41b are not limited to the embodiment shown in FIG. 4.

Furthermore, the contact part 32 of the connector 13 is provided on the fitting portion 42, and the contact part 34 of the connector 14, which is connected to the contact part 32 of the connector 13, is provided in the fitting portion 43. Since the contact part 32, which is electrically connected to the housing 36 of the processor device 3, is provided on the fitting portion 42 of the connector 13 that is covered with the recessed fitting portion 43 of the connector 14 as described above, the contact part 32 is not exposed to the outside in a state in which the connectors 13 and 14 are connected to each other, that is, during the use of the electronic endoscope apparatus 1. Accordingly, it is possible to prevent the electric shock of a user by preventing the user of the electronic endoscope apparatus 1 from coming into contact with the contact part 32.

Preferably, the contact part 32 is provided on the outer peripheral surface of the fitting portion 42 as in the embodiment shown in FIG. 3. According to this, since it is possible to increase the contact area between the contact parts 32 and 34, it is possible to more reliably electrically connect the ground of the electronic endoscope 2 to the housing 36 of the processor device 3.

Figure 5:
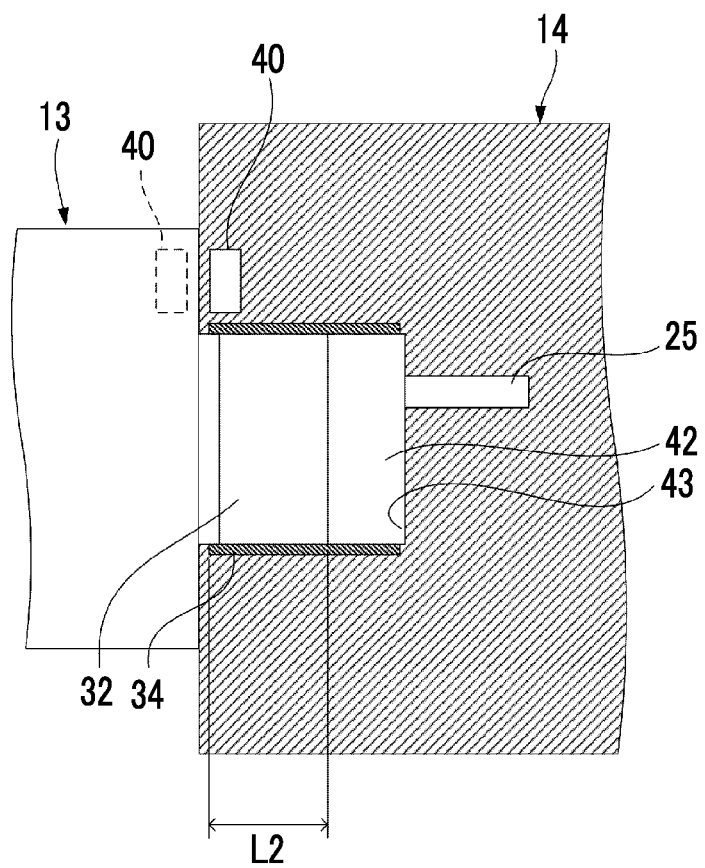
FIG. 5 is a schematic view showing a state in which the respective connectors of the electronic endoscope and the processor device of FIG. 3 are connected to each other.
Figure 6:
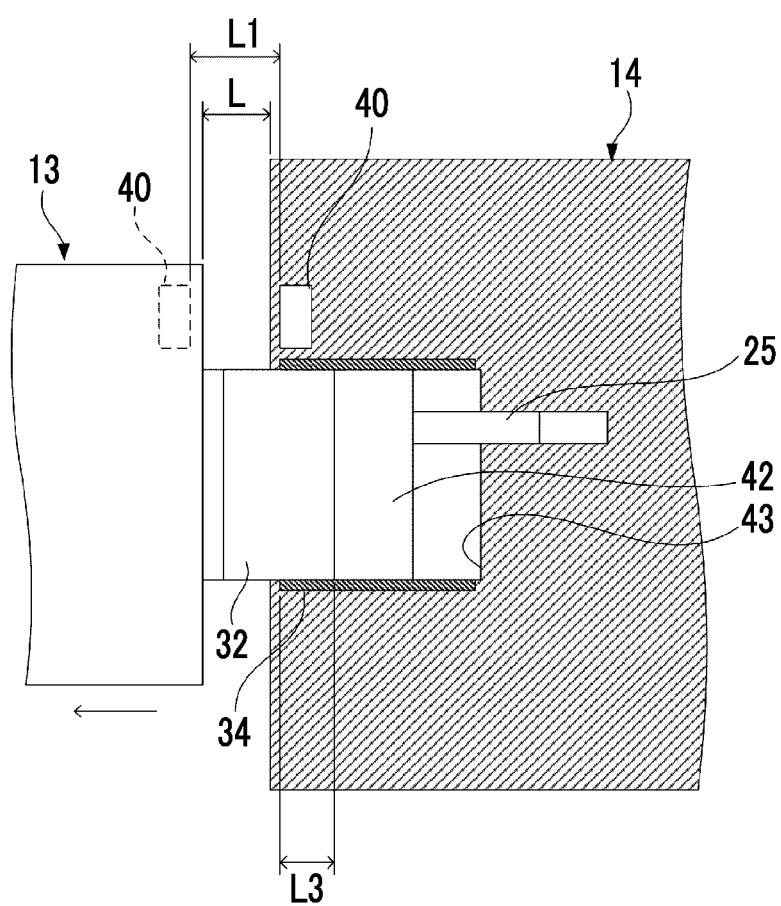
FIG. 6 is a schematic view showing a state in which the connection between the respective connectors of the electronic endoscope and the processor device of FIG. 3 is being released.

FIG. 5 shows a state in which the connectors 13 and 14 are connected to each other, and FIG. 6 shows a state in which the connection between the connectors 13 and 14 is being released.

In a state in which the connectors 13 and 14 are connected to each other, the respective coils 40 of the connectors 13 and 14, which transmit and receive power, are disposed so as to face each other without being in contact with each other in a fitting direction in which the fitting portion 42 of the connector 13 and the fitting portion 43 of the connector 14 are fitted to each other, and are electromagnetically coupled with each other. Further, the contact part 32 of the connector 13 and the contact part 34 of the connector 14 come into contact with each other.

When the connection between the connectors 13 and 14 is to be released, the connector 13 of the electronic endoscope 2 is typically moved in the fitting direction in which the fitting portion 42 of the connector 13 and the fitting portion 43 of the connector 14 are fitted to each other. Accordingly, the connection between the connectors 13 and 14 is released.

The respective coils 40 of the connectors 13 and 14 are separated from each other in the direction of the relative movement of the connector 13 with the relative movement of the connector 13 when the connection between the connectors 13 and 14 is released. Further, when a distance between the respective coils 40 of the connectors 13 and 14 exceeds the maximum distance that allows the transmission and reception of power to be maintained, the electromagnetic coupling between the coils 40 is released. For this reason, the transmission and reception of power become impossible. The maximum distance between the coils 40 also depends on current flowing in the coil 40 of the connector 14, the size of each of the coils 40 of the connectors 13 and 14, and the like; but is about 10 mm.

The electronic endoscope apparatus 1 is adapted so that the contact between the contact parts 32 and 34 is released after the electromagnetic coupling between the coils 40 is released and the transmission and reception of power become impossible. Specifically, when the maximum distance between the coils 40, which allows the transmission and reception of power to be maintained, in the direction of the relative movement of the connector 13 is denoted by L1, a distance between tip portions of the contact parts 32 and 34 in a state in which the connectors 13 and 14 are connected to each other is denoted by L2, and the relative moving distance of the connector 13 until the distance between the coils 40 reaches the maximum distance L1 from a state in which the connectors 13 and 14 are connected to each other is denoted by L, the electronic endoscope apparatus 1 is adapted so as to satisfy "L2>L".

Since the contact between the contact parts 32 and 34 is maintained by the above-mentioned structure when the distance between the coils 40 exceeds the maximum distance L1 with the relative movement of the connector 13 and the electromagnetic coupling between the coils 40 is released, the electrical connection between the ground of the electronic endoscope 2 and the ground of the processor device 3 is maintained. Accordingly, since the ground of the electronic endoscope 2 is kept at a reference potential when the electromagnetic coupling between the coils 40 is released and the transmission and reception of power become impossible, residual charge remaining in the imaging device 22 can be discharged along an assumed path and at an assumed timing. Therefore, it is possible to prevent the malfunction of the imaging device 22.

Since the operation of the imaging device 22 is stopped at the same time as the release of the electromagnetic coupling between the coils 40 in the electronic endoscope 2 of the electronic endoscope apparatus 1 on which an internal power supply is not mounted, shutdown processing for discharging residual charge cannot be performed. Accordingly, discharging residual charge as assumed by keeping the electrical connection between the ground of the electronic endoscope 2 and the ground of the processor device 3 is particularly useful.

It is preferable that a difference between the distance L2 between the tip portions and the relative moving distance L, that is, a contact length L3 between the contact parts 32 and 34 when the electromagnetic coupling between the coils 40 is released is 20 mm or more. Time, which is required to discharge residual charge, also depends on the circuit of the electronic device, and is typically in the range of several tens ms to several hundred ms. If the contact length L3 is 20 mm or more, it is possible to ensure time, which is sufficient to discharge residual charge, until the contact between the contact parts 32 and 34 is released after the release of the electromagnetic coupling between the coils 40 in consideration of the fact that the relative movement speed of the connector 13 at the time of the release of the connection between the connectors 13 and 14 is generally in the range of 100 mm/s to 200 mm/s. The upper limit of the contact length L3 between the contact parts 32 and 34 is not particularly limited in terms of the extension of time until the release of the contact between the contact parts 32 and 34. Considering the size of the connector, it is appropriate that the upper limit of the contact length L3 is 30 mm or less.

Figure 7:
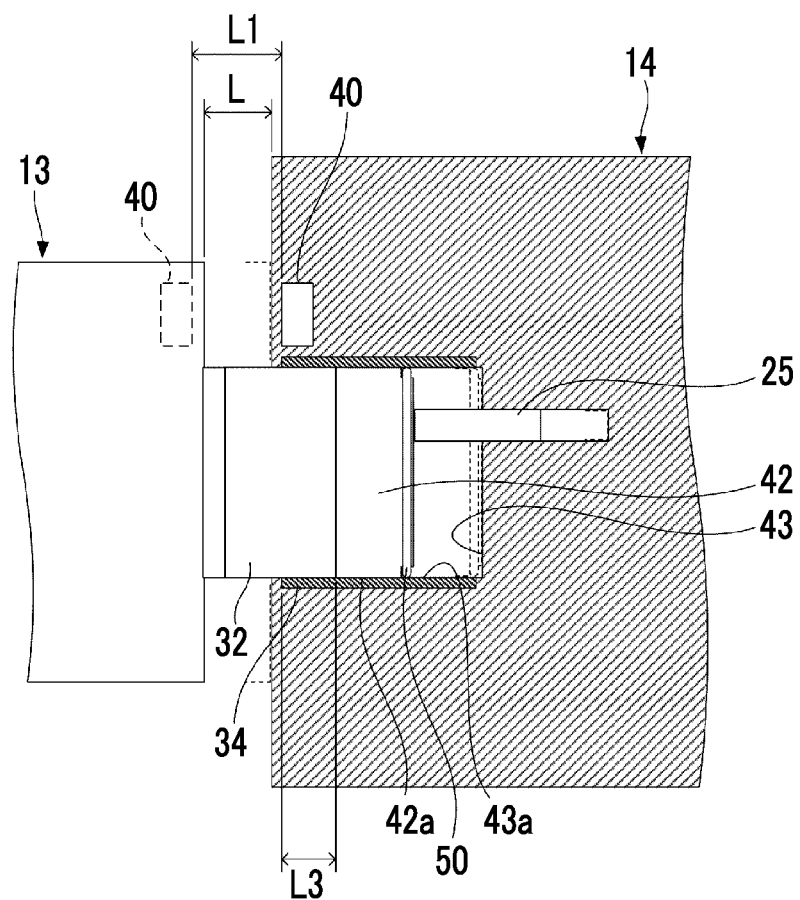
FIG. 7 is a schematic view showing the structure of a modification example of the respective connectors of the electronic endoscope and the processor device of FIG. 3.

FIG. 7 shows the structure of a modification example of the connectors 13 and 14.

In the modification example shown in FIG. 7, at least one connector of the connectors 13 and 14 is provided with a friction body that slides on the other connector. In the modification example shown in FIG. 7, an O-ring 50 as the friction body is provided at an edge portion, which is close to a tip, of an outer peripheral surface 42a of the fitting portion 42 of the connector 13. The O-ring 50 slides on an inner peripheral surface 43a of the fitting portion 43 of the connector 14 with the relative movement of the connector 13 when the connectors 13 and 14 are connected to each other or the connection between the connectors 13 and 14 is released.

Since the O-ring 50 slides on the inner peripheral surface 43a of the fitting portion 43 of the connector 14 with the relative movement of the connector 13 when the connection between the connectors 13 and 14 is released, frictional resistance with respect to the relative movement of the connector 13 is generated. Accordingly, it is possible to reduce the relative movement speed of the connector 13 when the connection between the connectors 13 and 14 is released. Therefore, since it is possible to reduce the contact length L3 between the contact parts 32 and 34 when the electromagnetic coupling between the coils 40 is released, it is possible to reduce the sizes of the connectors 13 and 14.

The O-ring 50 may be provided on the inner peripheral surface 43a of the fitting portion 43 of the connector 14, and the O-ring 50 may be provided on each of both the outer peripheral surface 42a of the fitting portion 42 and the inner peripheral surface 43a of the fitting portion 43. Further, the friction body may be a C-ring, and may be a member extending in the fitting direction (axial direction) in which the fitting portions 42 and 43 are fitted to each other instead of a member that extends in the circumferential direction on the outer peripheral surface 42a of the fitting portion 42 like the O-ring or the C-ring. Furthermore, the friction body may be provided, for example, at the end portion of the light guide 25 held by the fitting portion 42 or in a receiving portion of the processor device 3 that receives the end portion of the light guide 25, without being limited to the fitting portions 42 and 43.

Figure 8:
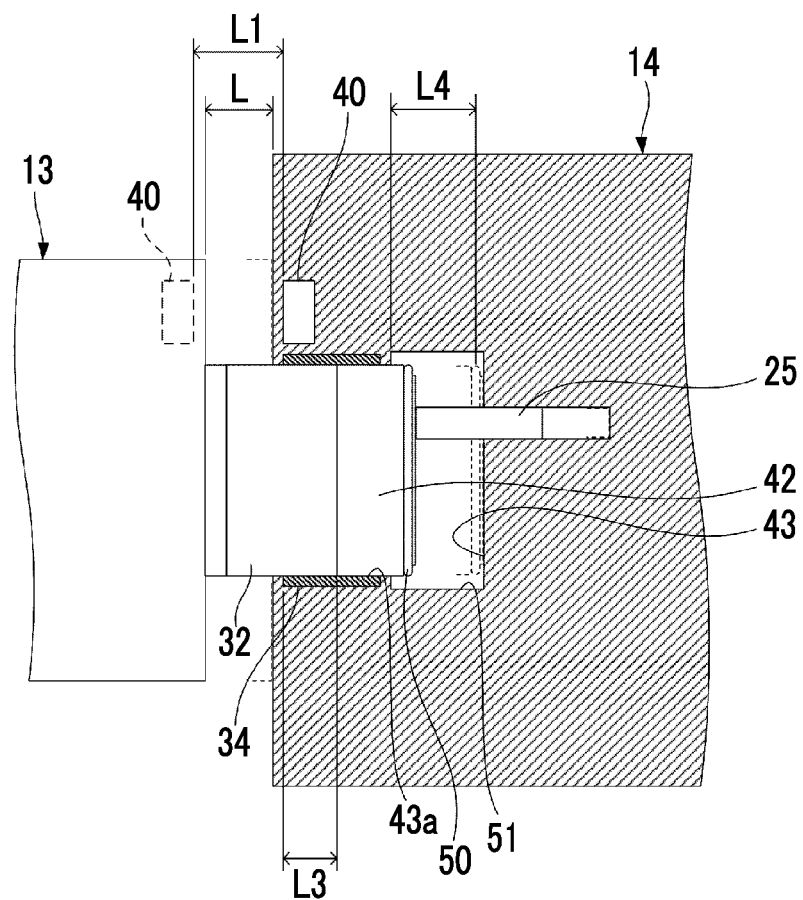
FIG. 8 is a schematic view showing the structure of another modification example of the respective connectors of the electronic endoscope and the processor device of FIG. 3.

FIG. 8 shows the structure of another modification example of the connectors 13 and 14.

In the modification example shown in FIG. 7, the O-ring 50 slides on the inner peripheral surface 43a of the fitting portion 43 until the completion of the removal of the fitting portion 42 from the fitting portion 43 and frictional resistance with respect to the relative movement of the connector 13 is generated. That is, frictional resistance is also generated with respect to the relative movement of the connector 13 until the distance between the coils 40 reaches the maximum distance L1. In contrast, the modification example shown in FIG. 8 is adapted so that frictional resistance is not generated with respect to the relative movement of the connector 13 until the distance between the coils 40 reaches the maximum distance L1 and frictional resistance is generated with respect to only the relative movement of the connector 13 after the distance between the coils 40 reaches the maximum distance L1.

In the modification example shown in FIG. 8, an annular recessed groove 51 is provided on a portion, which is close to the bottom, of the inner periphery of the fitting portion 43 of the connector 14. In a state in which the connectors 13 and 14 are connected to each other, the recessed groove 51 overlaps the O-ring 50 provided at the tip portion of the fitting portion 42 of the connector 13 and is formed so as to extend from the O-ring 50 toward the opening of the fitting portion 43. A gap L4, which is equal to or longer than the relative moving distance L (the relative moving distance of the connector 13 until the distance between the coils 40 reaches the maximum distance L1 from the state in which the connectors 13 and 14 are connected to each other) and shorter than the distance L2 between the tip portions, is formed between the O-ring 50 and the inner peripheral surface 43a of the fitting portion 43 as a sliding-target portion, on which the O-ring 50 slides, in the direction of the relative movement of the connector 13 when the connection between the connectors 13 and 14 is released.

When the connection between the connectors 13 and 14 is released, the O-ring 50 slides on the inner peripheral surface 43a of the fitting portion 43 after the distance between the coils 40 reaches the maximum distance L1. That is, frictional resistance is not generated with respect to the relative movement of the connector 13 until the distance between the coils 40 reaches the maximum distance L1 and frictional resistance is generated with respect to only the relative movement of the connector 13 after the distance between the coils 40 reaches the maximum distance L1. Accordingly, it is possible to improve operability when the connection between the connectors 13 and 14 is released.

Figure 9:
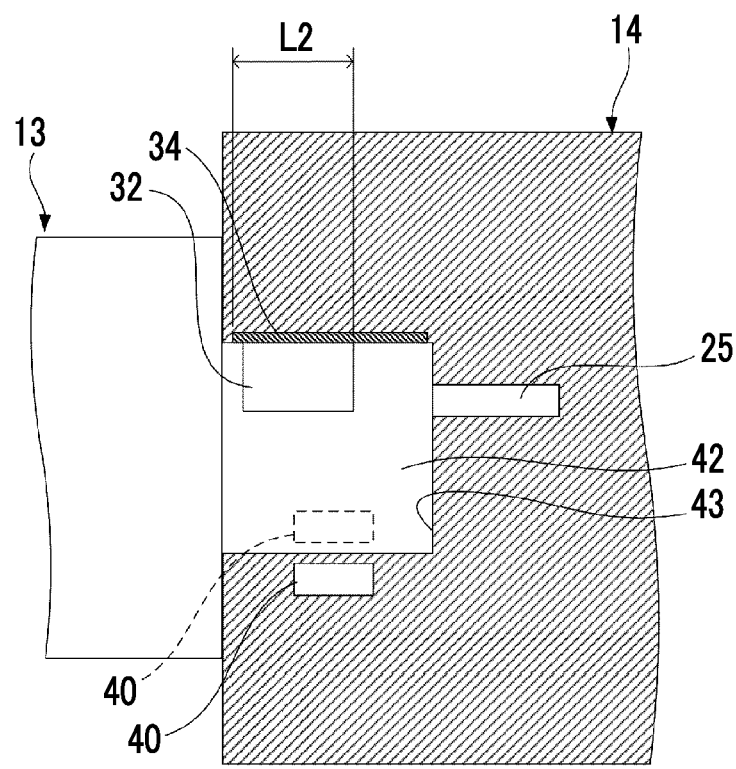
FIG. 9 is a schematic view showing the structure of another modification example of the respective connectors of the electronic endoscope and the processor device of FIG. 3 and showing a state in which the connectors are connected to each other.
Figure 10:
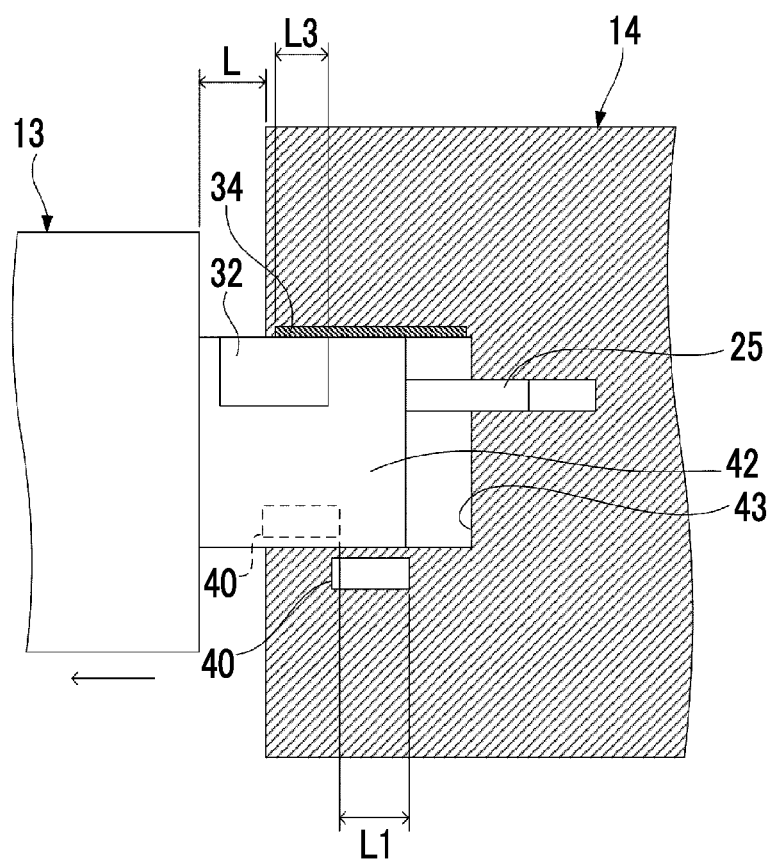
FIG. 10 is a schematic view showing a state in which the connection between the connectors of FIG. 9 is being released.

FIGS. 9 and 10 show the structure of another modification example of the connectors 13 and 14.

In the modification example shown in FIGS. 9 and 10, the coil 40 of the connector 13 is provided in the fitting portion 42, the coil 40 of the connector 14 is provided in the fitting portion 43, and both the coils 40 are disposed so as to face each other in a direction substantially orthogonal to the fitting direction in which the fitting portions 42 and 43 are fitted to each other.

When the maximum distance between the coils 40, which allows the transmission and reception of power to be maintained, in the direction of the relative movement of the connector 13 when the connection between the connectors 13 and 14 is released is denoted by L1, a distance between tip portions of the respective contact parts 32 and 34 in a state in which the connectors 13 and 14 are connected to each other is denoted by L2, and the relative moving distance of the connector 13 until the distance between the coils 40 reaches the maximum distance L1 from a state in which the connectors 13 and 14 are connected to each other is denoted by L, the electronic endoscope apparatus is adapted so as to satisfy "L2>L" even in the above-mentioned structure. Accordingly, after the electromagnetic coupling between the coils 40 is released and the transmission and reception of power become impossible, the contact between the contact parts 32 and 34 is released. Therefore, since the ground of the electronic endoscope 2 is kept at a reference potential when the electromagnetic coupling between the coils 40 is released and the transmission and reception of power become impossible, residual charge remaining in the imaging device 22 can be discharged along an assumed path and at an assumed timing. As a result, it is possible to prevent the malfunction of the imaging device 22. A structure, which comprises the O-ring 50 (the friction body) shown in FIGS. 7 and 8, can also be applied to this modification example.

Further, the electronic endoscope apparatus 1, which transmits and receives power between the electronic endoscope 2 and the processor device 3 while insulation between the electronic endoscope 2 and the processor device 3 is maintained by using the pair of coils 40 electromagnetically coupled with each other, has been described up to here. The invention is also useful for an electronic endoscope apparatus that transmits and receives power between the electronic endoscope 2 and the processor device 3 while insulation between the electronic endoscope 2 and the processor device 3 is maintained by using a pair of terminals coupled with each other by contact. Accordingly, when the electronic endoscope apparatus is adapted so that the contact between contact parts for electrically connecting the ground of the electronic endoscope to the ground of the processor device is released after the coupling between the pair of terminals is released and the transmission and reception of power become impossible, residual charge remaining in an electronic device mounted on the electronic endoscope can be discharged along an assumed path and at an assumed timing. As a result, it is possible to prevent the malfunction of the electronic device.

The followings will be disclosed in this specification as described above.

(1) An electronic endoscope apparatus comprising:
an electronic endoscope; and
a processor device that transmits and receives power and signals between the electronic endoscope and itself,
wherein the electronic endoscope and the processor device have connectors that are connected to each other, respectively,
the connectors include input/output units that transmit and receive power and signals, and contact parts that electrically connect a ground of the electronic endoscope to a ground of the processor device, and
when connection between the connectors is released, contact between the contact parts is released after coupling between the input/output units is released and the transmission and reception of power become impossible.

(2) The electronic endoscope apparatus according to (1), wherein the input/output units transmit and receive power and signals in a state in which the input/output units are insulated from each other.

(3) The electronic endoscope apparatus according to (2), wherein when the maximum distance between the input/output units, which allows the transmission and reception of power to be maintained, in a direction of a relative movement of the connector of the electronic endoscope when the connection between the connectors is released is denoted by L1, a distance between tip portions of the respective contact parts in a state in which the connectors are connected to each other is denoted by L2, and a relative moving distance of the connector of the electronic endoscope until the distance between the input/output units reaches the maximum distance L1 from a state in which the connectors are connected to each other is denoted by L, "L2>L" is satisfied.

(4) The electronic endoscope apparatus according to (3), wherein a difference between the distance L2 between the tip portions and the relative moving distance L is 20 mm or more.

(5) The electronic endoscope apparatus according to any one of (1) to (4),
wherein at least one connector of the connectors has a friction body that slides on the other connector.

(6) The electronic endoscope apparatus according to (5), wherein a gap, which is equal to or longer than the relative moving distance L and shorter than the distance L2 between the tip portions, is formed between the friction body and a sliding-target portion of the other connector, on which the friction body slides, in the direction of the relative movement of the connector of the electronic endoscope when the connection between the connectors is released.

(7) The electronic endoscope apparatus according to any one of (1) to (6),
wherein the electronic endoscope is an electronic endoscope on which an internal power supply is not mounted.

EXPLANATION OF REFERENCES

1: electronic endoscope apparatus
2: electronic endoscope
3: processor device
4: monitor
10: insertion part
11: operation part
12: universal cord
13: connector
14: connector
20: illumination optical system
21: objective optical system
22: imaging device
24: light source
25: light guide
28: imaging element
29: drive/readout circuit
30: wiring group
31: input/output unit
32: contact part
33: input/output unit
34: contact part
35: circuit unit
36: housing (ground)
37: power supply circuit
38: signal processing circuit
40: coil
41a: light-emitting element
41b: light-receiving element
42: fitting portion
42a: outer peripheral surface
43: fitting portion
43a: inner peripheral surface (sliding-target portion)
50: O-ring (friction body)
51: recessed groove
C1: capacitor

What is claimed is:

1. An electronic endoscope apparatus comprising:
an electronic endoscope; and
a processor device that transmits and receives power and signals between the electronic endoscope and itself,
wherein the electronic endoscope and the processor device have connectors that are connected to each other, respectively,
the connectors include input/output units including coils that transmit and receive power and including a light-emitting element and a light-receiving element that transmit and receive signals, and contact parts that electrically connect a ground of the electronic endoscope to a ground of the processor device,
wherein the input/output units transmit and receive power and signals in a state in which the input/output units are insulated from each other, and
wherein when the maximum distance between the input/output units, which allows the transmission and reception of power to be maintained, in a direction of a relative movement of the connector of the electronic endoscope when the connection between the connectors is released is denoted by L1, a distance between tip portions of the respective contact parts in a state in which the connectors are connected to each other is denoted by L2, and a relative moving distance of the connector of the electronic endoscope until the distance between the input/output units reaches the maximum distance L1 from a state in which the connectors are connected to each other is denoted by L, "L2>L" is satisfied,
when connection between the connectors is released, contact between the contact parts is released after coupling between the input/output units is released and the transmission and reception of power become impossible.

2. The electronic endoscope apparatus according to claim 1,
wherein a difference between the distance L2 between the tip portions and the relative moving distance L is 20 mm or more.

3. The electronic endoscope apparatus according to claim 2,
wherein at least one connector of the connectors has a friction body that slides on the other connector.

4. The electronic endoscope apparatus according to claim 3,
wherein a gap, which is equal to or longer than the relative moving distance L and shorter than the distance L2 between the tip portions, is formed between the friction body and a sliding-target portion of the other connector, on which the friction body slides, in the direction of the relative movement of the connector of the electronic endoscope when the connection between the connectors is released.

5. The electronic endoscope apparatus according to claim 4,
wherein the electronic endoscope is an electronic endoscope on which an internal power supply is not mounted.

6. The electronic endoscope apparatus according to claim 3,
wherein the electronic endoscope is an electronic endoscope on which an internal power supply is not mounted.

7. The electronic endoscope apparatus according to claim 2,
wherein the electronic endoscope is an electronic endoscope on which an internal power supply is not mounted.

8. The electronic endoscope apparatus according to claim 1,
wherein at least one connector of the connectors has a friction body that slides on the other connector.

9. The electronic endoscope apparatus according to claim 8,
wherein a gap, which is equal to or longer than the relative moving distance L and shorter than the distance L2 between the tip portions, is formed between the friction body and a sliding-target portion of the other connector, on which the friction body slides, in the direction of the relative movement of the connector of the electronic endoscope when the connection between the connectors is released.

10. The electronic endoscope apparatus according to claim 9,
wherein the electronic endoscope is an electronic endoscope on which an internal power supply is not mounted.

11. The electronic endoscope apparatus according to claim 8, wherein the electronic endoscope is an electronic endoscope on which an internal power supply is not mounted.

12. The electronic endoscope apparatus according to claim 1,
wherein the electronic endoscope is an electronic endoscope on which an internal power supply is not mounted.

* * * * *